United States Patent [19]

Knöfel et al.

[11] Patent Number: 4,675,437

[45] Date of Patent: Jun. 23, 1987

[54] CYCLOALIPHATIC TRIISOCYANATES

[75] Inventors: Hartmut Knöfel, Odenthal; Stefan Penninger, Pulheim; Michael Brockelt, Bergisch-Gladbach; Günter Hammen, Rommerskirchen; Herbert Stutz, Dormagen, all of Fed. Rep. of Germany

[73] Assignee: Bayer Aktiengesellschaft, Leverkusen, Fed. Rep. of Germany

[21] Appl. No.: 728,357

[22] Filed: Apr. 29, 1985

[30] Foreign Application Priority Data

May 12, 1984 [DE] Fed. Rep. of Germany ....... 3417683

[51] Int. Cl.⁴ .......................................... C07C 119/045
[52] U.S. Cl. .................................. 560/330; 560/347
[58] Field of Search .................... 260/453 A; 560/330

[56] References Cited

U.S. PATENT DOCUMENTS 3,330,850 7/1967 Campbell et al. ............. 260/453 A
3,557,180 1/1971 Hoeschele ..................... 260/453 A

FOREIGN PATENT DOCUMENTS 1171097 7/1984 Canada .
0104531 4/1984 European Pat. Off. .
0104551 4/1984 European Pat. Off. .
1080739 8/1967 United Kingdom .

OTHER PUBLICATIONS

H. Wagner, H. F. Sarx, Lackkunstharze, 5th Edition, Carl Hanser Verlag, Munich (1971).
H. Kittel, Lehrbuch der Lacke und Beschichtungen, Verlag W. A. Colomb in der Hennemann GmbH, Berlin-Oberschwandorf (1973).
Kunststoff-Handbuch by G. W. Becker and D. Braun, Carl Hanser Verlag, Munich/Vienna (1983), vol. 7, "Polyurethane", pp. 541–543.

*Primary Examiner*—Dolph H. Torrence
*Attorney, Agent, or Firm*—Gene Harsh; Joseph C. Gil; Lyndanne M. Whalen

[57] ABSTRACT

Cycloaliphatic triisocyanates or isomer mixtures of such triisocyanates corresponding to the formula

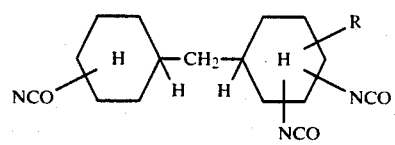

in which
R represents hydrogen or a $C_1$–$C_4$ alkyl group are produced by phosgenating the corresponding cycloaliphatic triamines or isomer mixtures of such triamines or a salt thereof.

These triisocyanates are useful in the production of polyisocyanate addition products, particularly polyurethane coatings and lacquers.

2 Claims, No Drawings

CYCLOALIPHATIC TRIISOCYANATES

BACKGROUND OF THE INVENTION

This invention relates to new cycloaliphatic triisocyanates and to a process for their production.

Aliphatic and cycloaliphatic diisocyanates such as 4,4'-diisocyanatodicyclohexyl methane, 3-isocyanatomethyl-3,5,5-trimethyl cyclohexyl isocyanate and hexamethylene diisocyanate are used industrially for the production of light-stable coating materials having excellent weather resistance. (See H. Wagner, H. F. Sarx, Lackkunstharze, 5th Edition, Carl Hanser Verlag, Munich (1971), 153 et. seq., H. Kittel, Lehrbuch der Lacke und Beschichtungen, Verlag W. A. Colomb in der Hennemann, GmbH, Berlin-Oberschwandorf (1973)).

However, isocyanates of low molecular weight have a high vapor pressure and, in some cases, are toxic. They are therefore modified before use, for example by trimerization, biuretization or by prepolymerization through reaction with low molecular weight polyols in order to satisfy industrial hygiene requirements during further processing. Modification such as this produces compounds of higher molecular weight and higher functionality which compounds have virtually no vapor pressure (cf. for example, Kunststoff-Handbuch by G. W. Becker and D. Braun, Carl Hanser Verlag, Munich-/Vienna (1983), Vol. 7, "Polyurethane", pp. 541–543).

However, subsequent modification of the monomeric diisocyanates is attended by several disadvantages. The additional step of modification involves more work and additional costs especially since, in most cases, a technically elaborate procedure is required for separating the modified product from excess monomers. In addition, monomeric diisocyanates may be formed through resplitting during storage of the modified polyisocyanates. Also, the modified polyisocyanates are generally of relatively high viscosity and are only suitable to a limited extent, if at all, for low-solvent or solvent-free applications. In addition, they cannot be purified by distillation due to their low vapor pressure.

SUMMARY OF THE INVENTION

It is an object of the present invention to provide new cycloaliphatic triisocyanates.

It is also an object of the present invention to provide cycloaliphatic triisocyanates useful in the production of light-stable coating materials having excellent weather resistance.

It is another object of the present invention to provide a relatively simple process for the production of cycloaliphatic triisocyanates.

These and other objects which will be apparent to those skilled in the art are accomplished by the triisocyanates and isomeric mixtures of triisocyanates of the present invention corresponding to the formula

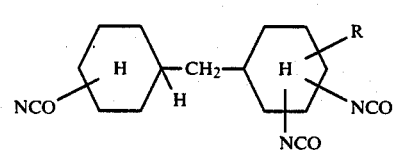

in which
R represents hydrogen or a $C_1$–$C_4$-alkyl group.

These isocyanates and their isomeric mixture are made by phosgenating triamines and isomeric mixtures of triamines corresponding to the formula

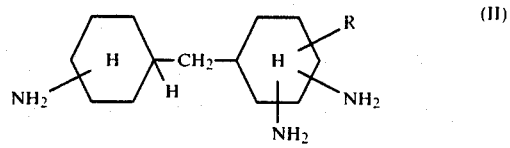

in which R is as defined above.

DETAILED DESCRIPTION OF THE INVENTION

The present invention relates to triisocyanates corresponding to the formula

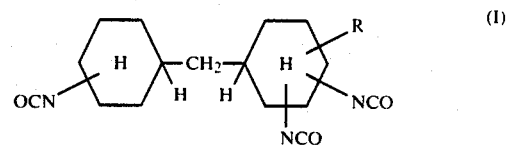

in which
R represents hydrogen or a $C_1$–$C_4$-alkyl radical, preferably hydrogen or a methyl group.

These triisocyanates may be in the form of position and/or stereo isomers.

The present invention also relates to a process for producing these triisocyanates in which the triamines on which they are based are phosgenated by methods known to those skilled in the art.

Finally, the invention also relates to the use of the triisocyanates of the present invention as a synthesis component in the production of polyisocyanate addition products, particularly, polyurethane plastics by the isocyanate polyaddition process. These triisocyanates may be reacted with any of the isocyanate-reactive group containing materials known to those in the art.

Starting materials for the phosgenation process of the present invention are the triamines corresponding to the triisocyanates which triamines correspond to the formula

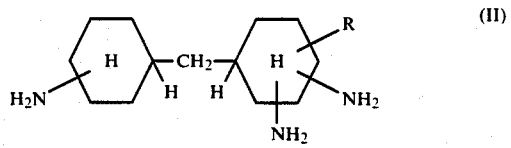

in which R is as already defined.

Starting materials for the production of the polyamines corresponding to formula (II) used in the process of the invention are the corresponding aromatic triamines represented by the following formula

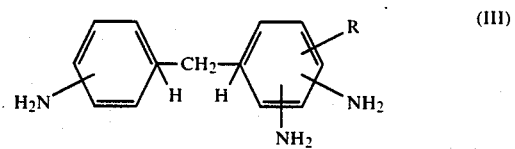

in which
R is as already defined.

These aromatic triamines may be produced in known manner. For example, N-[4(2)-aminobenzyl]-aniline may be reacted with optionally alkyl-substituted phenylene diamines in accordance with Beilstein 13H, page 309 or in accordance with German Patentschrift No. 107,718. The aromatic triamines may also be produced by reacting (i) a 3- or 4-nitrobenzyl halide, benzyl alcohol or a nitrobenzyl chloride isomer mixture with (ii) nitrobenzene, alkyl-substituted nitrobenzene, alkyl benzene or benzene in the presence of a Friedel-Crafts or acid catalyst, nitrating the reaction products thus obtained to form the corresponding trinitro compounds and hydrogenating the nitro groups in accordance with European Patent Application No. 46,917. The trinitro compounds obtained by the last of the above-mentioned methods and the aromatic triamines produced from them are, by the nature of their production, technical mixtures which, in addition to the corresponding trifunctional compounds, may also contain difunctional compounds. However, the difunctional compounds present in those mixtures may, if desired, be removed by distillation at the amine stage.

Typical examples of suitable starting materials represented by formula (III) are 2,4,4′(2′)-triaminodiphenyl methane, 2,6,4′(2′)-triamino-diphenyl methane, 4,6,4′(2′)-triamino-3-methyl diphenyl methane, 2,6,4′(2′)-triamino-3-methyl diphenyl methane, 3,5,4′(2′)-triamino-4-methyl diphenyl methane, 2,6,4′(2′)-triamino-4-methyl diphenyl methane, 3,5,4′(2′)-triamino-2-methyl diphenyl methane, 4,6,4′(2′)-triamino-2-methyl diphenyl methane and mixtures thereof. The corresponding ethyl-, isopropyl-, n-propyl- or n-, iso- or tert.-butyl-substituted triaminodiphenyl methanes may also be used.

However, preferred starting materials are isomer mixtures of methyl-substituted triaminodiphenyl methanes or technical mixtures thereof with the corresponding diamines, of the type which accumulate in the trinitration of 2- and/or 4-methyl diphenyl methane or hydrocarbon mixtures made up of those isomers, reduction of the nitro groups, and optionally, subsequent, working-up by distillation. The particularly preferred starting materials obtained by this method generally contain more than 80 wt. % of triaminodiphenyl methanes of which more than 90 wt. % are made up of aminobenzyl diaminotoluene isomers.

The starting materials may be exclusively aromatic triamines corresponding to formula (III) and/or mixtures of those triamines or even mixtures of those triamines with the corresponding diamines which diamines preferably contain an amino group on each aromatic ring. These mixtures may contain up to 90 wt. %, preferably up to 50 wt. % and, more preferably, up to 20 wt. %, based on the mixture as a whole, of those diamines. Polyamine mixtures which, due to the method of their production, have a high content of aromatic diamines, may be completely or substantially completely freed from the diamines by distillation before they are hydrogenated to form the starting materials for the phosgenation process of the present invention. However, it is also possible to subject the aromatic polyamines as such to hydrogenation and then to free the hydrogenated polyamine mixtures from the diamines and other secondary products formed during hydrogenation. Finally, it is also possible, on completion of the phosgenation process of the present invention, to separate off difunctional end products (obtained through phosgenation of the corresponding diamines) and other secondary products, if any, by distillation in order to obtain substantially pure polyisocyanates corresponding to formula (I).

The nucleus hydrogenation of the aromatic polyamines corresponding to formula (III) is generally carried out by known methods (See P. Rylander, Catalytic Hydrogenation in Organic Syntheses, Academic Press New York, San Francisco, London (1979), page 190). The aromatic amines are catalytically hydrogenated until all of the hydrogen has been taken up. Hydrogenation is carried out at 20° to 300° C. under a pressure of from 100 to 300 bars and preferably at 150° to 250° C. under a pressure of from 70 to 300 bars, more preferably under a pressure of from 120 to 300 bars.

Hydrogenation is carried out in the presence of from 0.1 to 30 wt. % and preferably in the presence of from 0.1 to 10 wt. % (based on catalytically active metal and diamino compound) of a hydrogenation catalyst. Suitable catalysts are elements of the 8th Secondary Group of the Periodic System of Elements optionally applied to inert supports, such as active carbon, silica gel, calcium carbonate, barium sulfate and, in particular, aluminum oxide, as well as catalytically active inorganic compounds of those elements.

Particularly suitable catalysts include: ruthenium, platinum, rhodium, nickel and/or cobalt catalysts in elemental or chemically combined form. Particular preference is attributed to ruthenium or catalytically active ruthenium compounds. Examples of suitable ruthenium compounds are ruthenium oxide; barium perruthenite; sodium, potassium, silver, calcium and magnesium ruthenate; sodium perruthenate; ruthenium pentafluoride; ruthenium tetrafluoride hydrate and ruthenium trichloride. If supports for the catalyst are used, the metal content of the supported catalyst generally amounts to between 1 and 10 wt. % and preferably to between 1 and 5 wt. %. The quantity and type of catalyst used are of course not crucial in any sense to the hydrogenation reaction.

It is often advisable to carry out the hydrogenation reaction in the presence of ammonia because undesirable deamination reactions and the formation of secondary amines as secondary products can be suppressed by the presence of ammonia. If ammonia is used, the quantities used generally amount to between 0.1 and 30 wt. % and preferably to between 5 and 10 wt. %, based on the starting materials to be hydrogenated.

Hydrogenation may be carried out in the absence of solvents or in the presence of inert solvents. In general, low-melting or liquid aromatic amines are hydrogenated as such while high-melting diamines are hydrogenated in solution. Suitable solvents are low-boiling compounds which are inert under the reaction conditions, preferably alcohols, such as methanol, t-butanol, ethanol, n-propanol, i-propanol; ethers such as dioxane, tetra-hydrofuran, diethyl ether and hydrocarbons, such as cyclohexane.

The hydrogenation reaction may be carried out continuously in a tube reactor or in a cascade of pressure vessels. It is preferred that hydrogenation be carried out in batches in a stirrer-equipped autoclave by charging the autoclave with catalyst, the substance to be hydrogenated and a solvent (if any), repeatedly purging the autoclave with inert gas and optionally introducing ammonia. Thereafter hydrogen is introduced under pressure, the mixture is heated to the reaction temperature, hydrogenated until the pressure remains constant and then stirred for about another 0.5 to 5 hours at the same temperature. After cooling of the reaction mixture and separation of the catalyst, the hydrogenation product is generally worked up by distillation.

The hydrogenation products accumulate in high yields and, as already mentioned, may be freed if necessary from secondary products by distillation. Even after they have thus been purified by distillation, the triamines are generally mixtures of stereo- and, optionally, position-isomers. Working up by distillation as described above gives triamines of which more than 80 wt. % and preferably more than 90 wt. % are triamines corresponding to general formula (II). However, even the hydrogenation products which are not worked up by distillation represent triamines within formula (II) even though they may be mixtures of position and/or stereo isomers or present in admixture with up to 90 wt. %, preferably with up to 50 wt. % and, more preferably, with up to 40 wt. % of other, optionally alkyl-substituted di- and/or triamines having a diphenyl methane, benzyl cyclohexane or dicyclohexyl methane structure. Such diamines may be present in cases where the starting materials used are aromatic triamines which contain aromatic diamines and/or in cases where the cycloaliphatic ring undergoes slight deamination during the hydrogenation reaction. However, deamination may be suppressed by the presence of ammonia during the hydrogenation reaction. Monoamines may even form in very small quantities through deamination. However, they may be removed very easily by distillation. In the event of incomplete hydrogenation, polyamines having a diphenyl methane or benzyl cyclohexane structure will be present in small quantities in the hydrogenation products but generally do not adversely affect their usefulness.

In general, there is no need for the hydrogenation products to be purified by distillation before they are used in the phosgenation process of the present invention because, as already mentioned, working up of the end products by distillation may be carried out after the phosgenation reaction. The suitability of the hydrogenation products for use in the phosgenation process of the present invention is unaffected by their position and stereo isomerism or by the isomer distribution.

Typical examples of suitable starting polyamines for the phosgenation process of the present invention are the cycloaliphatic triamines corresponding to the aromatic triamines mentioned above which have optionally been freed from the secondary products formed during the hydrogenation reaction by distillation. The starting polyamines used in the phosgenation process of the invention correspond substantially to the aromatic polyamines or polyamine mixtures from which they were produced.

In the practical application of the process of the present invention for producing the new triisocyanates, the phosgenation of the starting amines or their salts is carried out by methods known to those skilled in the art in the presence of an inert organic solvent (See Houben-Weyl, Methoden der organischen Chemie, Georg Thieme Verlag Stuttgart (1952), Vol. 8, 4th Edition, pages 120 et. seq). In this context, "starting amines" are understood to be both pure compounds of general formula (II), optionally as mixtures of position and stereo isomers, and also mixtures thereof with up to 90 wt. %, preferably with up to 50 wt. % and more preferably with up to 20 wt. % of other, optionally alkyl-substituted di- and/or triamines having a diphenyl methane, benzyl cyclohexyl or dicyclohexyl methane structure. The percentages given are based on the mixture as a whole.

Suitable salts which may be phosgenated are, preferably, hydrochlorides or ammonium carbamates which are formed by saturation of the polyamine solutions with gaseous hydrogen chloride or carbon dioxide. In principle, it is also possible to phosgenate other salts which are formed, for example, by neutralization of the polyamines with protons.

The selectivity of the phosgenation reaction is largely dependent upon the amine concentration and upon the excess of phosgene. Preferably, the phosgene is used in a large molar excess while the amines to be phosgenated are used in highly dilute form. In general, the molar excess of phosgene amounts to between 100 and 2000% and preferably to between 100 and 1000%. The concentration of amine, based on the total quantity of amine and solvent is generally between 0.1 and 15 wt. % and preferably between 5 and 10 wt. %.

The solvents used may be any inert organic liquids, or mixtures thereof, having boiling points in the range from 60° to 250° C., such as halogenated hydrocarbons, and aromatic materials, preferably chlorides. Examples of suitable solvents are xylene, mesitylene, chlorobenzene, dichlorobenzene, trichlorobenzene, chloronaphthalene and dichloroethane.

The reaction may be carried out either in a single stage by hot phosgenation at temperatures in the range from 100° to 250° C. or in two stages by cold/hot phosgenation at temperatures of from −20° to 250° C. and under normal pressure.

Where the free amines are used as starting compound (base phosgenation), ammonium carbamic acid chloride is first produced at temperatures in the range from −20° to +60° C. and is then further reacted with phosgene at 20° to 250° C. to form the polyisocyanate.

The end products of the process are generally purified after dephosgenation, by evaporating off the solvent, followed by distillation under reduced pressure.

The end products of the process of the present invention (i.e. the new triisocyanates) are obtained in high yields in the form of colorless to yellow, low-viscosity liquids. These triisocyanates are valuable synthesis components in the production of polyurethane plastics by the isocyanate-polyaddition process. The position and/or stereo isomerism of the new triisocyanates largely corresponds to the isomerism of the triamines used in the phosgenation reaction. In general, there is no need to separate the mixtures accumulating in the phosgenation process into individual position and/or stereo isomers because the end products may be used directly. Diisocyanates and other secondary products (particularly phosgenation products of triamines having a diphenyl methane or dicyclohexyl methane structure) optionally present in admixture with the triisocyanates corresponding to the formula (I) may be completely or partly separated off from the triamines by distillation. For many applications of the triisocyanates of the invention, however, there is no need for any such purification because even the corresponding polyisocyanate mixtures, which contain more than 50 wt. % and preferably more than 80% by weight of polyisocyanates of formula (I), represent valuable new starting materials for polyurethane chemistry. The triisocyanates of the present invention or mixtures thereof with the above-mentioned secondary products, which contain at least 50 wt. % and preferably at least 80 wt. % of triisocyanates of formula (I) may be used with particular advantage in the production of polyurethane lacquers and coating materials. The triisocyanates of the present invention may be used instead of or together with the polyisocyanates hitherto used in the process for producing such plastics known to those in the art.

One particular advantage of the polyisocyanates of the present invention over state-of-the-art lacquer-grade polyisocyanates lies in the fact that they are low-viscosity, distillable liquids. Nevertheless, the new triisocyanates have a sufficiently low vapor pressure to satisfy industrial hygiene requirements for the production of polyurethanes, particularly polyurethane lacquers.

The invention is illustrated by the following Examples in which all the percentages quoted are percentages by weight, unless otherwise indicated. Analysis of the isomer distribution of the intermediate and end products was carried out by gas chromatography.

EXAMPLES

EXAMPLE 1

1(a) A technical amine mixture made up of 1.4% of 4,4'-diaminodiphenyl methane, 10.2% of 4,6,2'-triamino-3-methyl diphenyl methane, 6.8% of 2,6,4'-triamino-3-methyl diphenyl methane, 78.7% of 4,6,4'-triamino-3-methyl diphenyl methane and 2.9% of the other aromatic polyamines, was obtained by reacting 2,4-diamino-toluene with industrially produced N-aminobenzyl aniline containing more than 80% of N-[4-aminobenzyl]aniline in the presence of hydrochloric acid (degree of protonation: 50%), followed by neutralization of the catalyst with sodium hydroxide and working up by distillation. 380 g of this amine mixture, 380 g of tert.-butanol and 76 g of ruthenium-aluminum oxide supported catalyst (5% Ru) were initially introduced into a 700 ml stirrer-equipped autoclave into which (after repeated purging with nitrogen and hydrogen) hydrogen was introduced under a pressure of 100 bars. The contents of the autoclave were heated first to 130° C. (melting point of the amine mixture), the stirrer was switched on and the temperature was increased to 200° C. Hydrogen was then introduced at a constant temperature under a pressure of 275 bars until, after 5.25 hours, the pressure in the autoclave remained constant. The autoclave contents were then cooled to around 60° C., after which the autoclave was vented and the crude product was taken up in methanol.

The catalyst was filtered under suction and the product was distilled. 364.4 g of an amine mixture having the following composition, as determined by gas chromatography, distilled over at a boiling temperature of 115°–170° C./0.9 mbar:

30.3% of diaminomethyl dicyclohexyl methane (isomer mixture),
61.3% of triaminomethyl dicyclohexyl methane (isomer mixture) and
8.4% of unidentified amines.

The triamines obtained were almost exclusively those containing one amino group on the cyclohexane ring containing no alkyl substituent and two amino groups on the methyl-substituted cyclohexane ring.

Another distillation cycle produced 164.0 g of a hydrogenation product boiling at 139°–170° C./0.1 mbar of which according to analysis by gas chromatography was 92.1% triaminomethyl dicyclohexyl methane isomers.

1(b) 95 g of the hydrogenation product purified by distillation in accordance with 1(a) were dissolved in 700 ml of dry chlorobenzene and carbon dioxide introduced into the resulting solution at 40°–45° C. up to saturation point. The suspension formed was run dropwise with intensive stirring at 0° C. into a solution of 250 g of phosgene in 700 ml of chlorobenzene. The reaction mixture was heated to boiling temperature while phosgene was introduced and boiled for 2 hours until the solids had completely dissolved. The reaction mixture was then phosgenated for another 3 hours during which phosgene was introduced at a rate of approximately 300 g/h. Excess phosgene was dispersed by injecting nitrogen into the solution for 1 hour at boiling temperature. The solvent was distilled off under a pressure of 1000 to 100 mbar and 107 g of crude isocyanate were obtained after flash distillation at 180°14 230° C./0.3–0.5 m bar. After redistillation, 105 g of triisocyanato-methyl dicyclohexyl methane of formula (I) (R=CH$_3$), in the form of an isomer mixture having an NCO-content of 38.6% were obtained in the form of a fraction distilling at 165°–170° C./0.05 mbar.

EXAMPLE 2

2(a) A 0.7 liter stirrer-equipped autoclave was charged with 14 g of ruthenium-aluminum oxide supported catalyst (5% Ru) and 350 g of a condensation product of N-(4(2)-aminobenzyl)-aniline and m-phenylene diamine having the following composition:

2.2% of m-phenylene diamine,
0.6% of 2,6,4'-triaminodiphenyl methane,
14.5% of 2,4,2'-triaminodiphenyl methane and
82.7% of 2,4,4'-triaminodiphenyl methane.

After repeated purging with nitrogen and hydrogen, 39 g of liquid ammonia were added. Hydrogen was introduced under a pressure of 100 bars and the autoclave was heated to 140° C. Hydrogenation was then carried out while stirring with 275 bars of hydrogen. The temperature was increased over a period of 23 h to 200° C. and hydrogenation continued for another 7 h at the same temperature. The autoclave was then allowed to cool to 60° C., vented and the catalyst was separated off by filtration under suction at 70° C. Distillation at 127°–185° C./0.4 mbar gave 337.5 g of a mixture of cycloaliphatic amines having the following compositions:

2.5% of monoaminodicyclohexyl methane (isomer mixture),
21.4% of diaminodicyclohexyl methane (isomer mixture),
74.6% of triaminodicyclohexyl methane (isomer mixture),
0.6% of 4(2,4-diaminobenzyl)-cyclohexyl amine and
0.9% of unidentified amines.

Redistillation at 127°–157° C./0.2–0.3 mbar gave 259.3 g of a mixture of various triamininodicyclohexyl methane isomers containing 8.5% of diaminodicyclohexyl methane. The triamines were those of the type which contain two amino groups on one cyclohexane ring and one amino group on the other cyclohexane ring as substituents.

2(b) 112.5 g of the hydrogenation product produced in accordance with 2(a) and purified by distillation were dissolved in 1900 ml of dry chlorobenzene. Carbon dioxide was introduced into the resulting solution to saturation point. A colorless suspension was formed and, after cooling to 0° C., was gassed while stirring with 600 g of phosgene. The suspension was then heated to 110° C. in 3 hours while phosgene was introduced at a rate of 150 g/h. After the solids had completely dissolved, the mixture was stirred under the same conditions for 4 hours.

After dephosgenation for 1 hour and removal of the solvent by distillation, the crude isocyanate was distilled at 180°-220° C./0.2-0.5 mbar. 130 g of crude product having an NCO-content of 39.1% were obtained. Redistillation at 174°-180° C./0.1-0.4 mbar gave 107 g of triisocyanato-dicyclohexyl methane corresponding to formula (I) (R=H), in the form of an isomer mixture having an NCO-content of 41% and a viscosity at 25° C. of 112 mPa.s.

EXAMPLE 3

3(a) An aromatic polyamine mixture made up of 2.6% of diaminotoluene (isomer mixture), 6.2% of diaminomethyl diphenylmethane (isomer mixture containing more than 90% of diamines of the type containing one amino substituent on each aromatic ring) and 91.2% of triamino-methyl diphenyl methane (isomer mixture containing more than 90% of triamines with one amino group on the unsubstituted aromatic ring and two amino groups on the methyl-substitued aromatic ring) was obtained by the nitration of methyl diphenyl methane, followed by catalytic hydrogenation using Raney nickel in accordance with European Patent Application No. 46,917. 350 g of this polyamine mixture were hydrogenated at 200° C./275 bars in accordance with Example 1(a) in the presence of 35 g of ruthenium (5%)/aluminum oxide supported catalyst and 35 g of ammonia in a 0.7 liter stirrer-equipped autoclave. After distillation twice, the hydrogenation product which was 91% triaminomethyl dicyclohexyl methane corresponding to formula (I) (R=CH$_3$), and 9% diaminomethyl dicyclohexyl methane, was isolated in a yield of 69.2 g (B.p. 132°-148° C./0.1 mbar).

3(b) 63 g of the distilled hydrogenation product of Example 3(a) were dissolved in 400 ml of dry chlorobenzene and the resulting solution was saturated with carbon dioxide.

The white suspension of ammonium carbamates which formed was run dropwise into a solution of 150 g (1.53) moles of phosgene in 400 ml of chlorobenzene while stirring at 0°-10° C. The suspension was then heated to reflux temperature while phosgene was introduced until, after boiling for about one hour a clear solution formed. After phosgenation for another 3 hours, excess phosgene was removed by the injection of nitrogen. After removal of the solvent by evaporation and flash distillation at 170°-200° C./0.1-0.3 mbar, 65 g of crude phosgenate were obtained. According to analysis by gas chromatography, 90% of the phosgenate was triisocyanatomethyl dicyclohexyl methane. Redistillation at 168°-175° C./0.1 mbar yielded 55 g of a polyisocyanate mixture of 96.7% triisocyanatomethyl dicyclohexyl methane corresponding to formula (I) (R=CH$_3$) in the form of an isomer mixture and 3.3% of diisocyanatomethyl dicyclohexyl methane isomers. The mixture had an NCO-content of 38.65% and a viscosity of 196 mPa.s/25° C.

EXAMPLE 4

4(a) 253 g (1.19 moles) of 2,4,4'-triaminodiphenyl methane obtained by recrystallization of the starting mixture described in Example 2 from 1,2-dichlorobenzene, 250 ml of tert.-butanol and 50.6 g of the catalyst described in Example 1 were introduced into a 1.3 liter stirrer-equipped autoclave. After repeated purging with nitrogen and hydrogen, 100 bars of hydrogen were introduced. The contents of the autoclave were heated to 180° C. and then hydrogenated with intensive stirring at 180° C./275 bars. The uptake of hydrogen was over after 105 minutes. The autoclave was cooled to 60° C., vented and the catalyst filtered off from the solution under suction. After removal of the solvent by distillation, the crude product was subjected to flash distillation at 115°-195° C./0.5 mbar and 238.3 g of distillate were obtained. 81.5% of the distillate was 2,4,4'-triamino-dicyclohexyl methane, 16.1% was diaminodicyclohexyl methane and the rest was undefined polyamines. Purification of this product by distillation yielded 175.4 g of 2,4,4'-triaminodicyclohexyl methane which contained 2.3% (based on the mixture as a whole) diaminodicyclohexyl methane (isomer mixture) and had a boiling point of 147° to 153° C./0.2 mbar.

4(b) 169 g of the hydrogenation product purified by distillation in accordance with Example 4(a) were dissolved in 2.5 liters of chlorobenzene and the resulting solution saturated with carbon dioxide. A suspension was formed. The suspension thus formed was cooled to −20° C., and 400 g of phosgene were introduced. After stirring for 15 minutes, the stream of phosgene was reduced to 15 l/h and the reaction mixture heated in 1 hour to boiling temperature. The reaction mixture was then stirred again. The solids dissolved completely in 2.5 hours. After another 3 hours, the stream of phosgene was stopped, nitrogen was introduced, excess phosgene was blown out and the solvent distilled off at 15 mbar. The crude product was then subjected to flash distillation under a vacuum of 1 mbar and analyzed by gas chromatography. 181 g of crude isocyanate were obtained. 86.8% (70.6% of the theoretical) was 2,4,4'-triisocyanato-dicyclohexyl methane, 9.0% was diisocyanatodicyclohexyl methane and 4.2% were unknown products. Redistillation at 180°-185° C./0.2 mbar yielded 162 g of isocyanate containing 95.5% of 2,2,4'-triisocyanatodicyclohexyl methane and 4.5% of diisocyanatodicyclohexyl methane isomers. The isocyanate had an NCO-content of 39.0% and a viscosity at 25° C. of 109 mPa.s.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A triisocyanate or isomeric mixture of triisocyanates corresponding to the formula

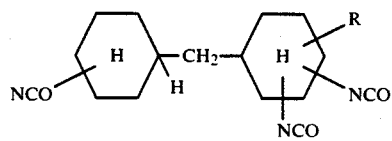

in which

R represents hydrogen or a C$_1$-C$_4$ alkyl group.

2. The triisocyanate or isomeric mixture of triisocyanates of claim 1 in which R represents hydrogen or a methyl group.

* * * * *